United States Patent [19]

Ramachandran

[11] Patent Number: 4,552,963

[45] Date of Patent: * Nov. 12, 1985

[54] PREPARATION OF 1-ALKYL-1,4-DIHYDRO-4-OXO-7-(4-PYRIDYL)-3-QUINOLINECARBOXYLIC ACID

[75] Inventor: Venkataraman Ramachandran, Baton Rouge, La.

[73] Assignee: Ethyl Corporation, Richmond, Va.

[*] Notice: The portion of the term of this patent subsequent to Nov. 12, 2002 has been disclaimed.

[21] Appl. No.: 497,026

[22] Filed: May 23, 1983

[51] Int. Cl.[4] ............... C07D 215/16; C07D 211/70; C07D 211/72

[52] U.S. Cl. .................................. 546/156; 546/329; 546/346

[58] Field of Search .................. 546/346, 156, 329

[56] References Cited

U.S. PATENT DOCUMENTS 4,405,792  9/1983  Walter ............................... 546/346

OTHER PUBLICATIONS

Conrow et al., Deductive Organic Chemistry, Addison-Wesley Pub. Co., Inc., Reading, Mass., 1966, p. 171.
Carruthers, "Some Modern Methods of Organic Synthesis" Cambridge Univ. Press, Cambridge, Eng., 2nd Ed., p. 198.

*Primary Examiner*—Henry R. Jiles
*Assistant Examiner*—Robert C. Whittenbaugh
*Attorney, Agent, or Firm*—Donald L. Johnson; John F. Sieberth; Patricia J. Hogan

[57] ABSTRACT

The yield of Diels-Alder product obtained by reacting a haloprene with a 4-vinylpyridine is increased by conducting the reaction in the presence of a boron trifluoride catalyst, preferably a boron trifluoride etherate. The product obtained by the reaction, a mixture of 4-(chlorocyclohex-3-enyl)pyridines, is useful in the production of antibacterial 1-alkyl-1,4-dihydro-4-oxo-7-pyridinyl-3-quinolinecarboxylic acids.

16 Claims, No Drawings

PREPARATION OF 1-ALKYL-1,4-DIHYDRO-4-OXO-7-(4-PYRIDYL)-3-QUINOLINECARBOXYLIC ACID

FIELD OF THE INVENTION

This invention relates to 4-(halocyclohex-3-enyl)pyridines, a process for preparing them, and processes for producing derivatives thereof.

BACKGROUND

U.S. Pat. No. 4,405,792—Walter I—discloses 4-(3-chlorocyclohex-3-enyl)pyridine, 4-(4-chlorocyclohex-3-eny)-pyridine, a process for making these compounds by a Diels-Alder reaction between chloroprene and a 4-vinylpyridine, and a process for converting them to 4-(3-chlorophenyl)pyridine and 4-(4-chlorophenyl)pyridine by catalytic dehydrogenation.

Copending application Ser. No. 495,977, filed May 19, 1983, in the name of Thomas J. Walter—Walter II—discloses processes by which 4-(4-halophenyl)pyridines, such as the 4-chlorophenyl)pyridine produced in Walter I, can be converted to 4-(4-halo-3-nitrophenyl)-pyridines, then to 4-(3-aminophenyl)pyridines, and ultimately to the antibacterial 1-alkyl-1,4-dihydro-4-oxo-7-pyridinyl-3-quinolinecarboxylic acids of Sterling Drug's U.S. Pat. Nos. 3,753,993 (Lesher et al.), 3,907,808 (Lesher and Carabateas), and 4,118,557 (Lesher).

Separately and in combination, the aforementioned copending applications disclose useful processes for preparing antibacterial agents and intermediates thereof. However, as indicated by the working examples of Walter I, it has not previously been known how to conduct a Diels-Alder reaction between chloroprene and 4-vinylpyridine, or homologs thereof, so as to get satisfactory yields of 4-(chlorocyclohex-3-enyl)pyridines. The side reactions that have occurred in the reaction, specifically the polymerization of the chloroprene and the dimerization of the 4-vinylpyridine, have reduced the yield to not more than about 20-30% of 4-(chlorocyclohex-3-enyl)pyridine isomers in a 65:35 mol ratio of 4-(4-chlorocylohex-3-enyl)pyridine to 4-(3-chlorocyclohex-3-enyl)-pyridine.

W. Carruthers, *Some modern methods of organic synthesis*, Second Edition, Cambridge University Press, 1978, page 198, shows that previous attempts to catalyze Diels-Alder reactions have generally met with little success but that some Diels-Alder reactions have been found to be accelerated remarkably by aluminum chloride and other Lewis acids. J. Sauer, "Diels-Alder Reactions II: The Reaction Mechanism," *Angewandte Chemie international Edition*, Volume 6, No. 1, 1967, pages 16-33, teaches that the acceleration of Diels-Alder reactions by Lewis acids, including boron trifluoride, can be considerable in some cases (page 28), that the ratio of stereoisomers produced by the reaction can be affected by the use of Lewis acids (page 19), and that the ratio of position isomers can also be affected (page 24).

It would be advantageous to be able to modify Diels-Alder reactions between haloprenes and 4-vinylpyridines so as to produce satisfactory yields of Diels-Alder adducts and concurrently to maximize the yield of the isomers most desirable for the production of the aforementioned antibacterial agents, i.e., the 4-(4-halocyclohex-3-enyl)pyridine isomers.

SUMMARY OF INVENTION

An object of this invention is to provide a novel Diels-Alder process for preparing 4-(halocyclohex-3-enyl)pyridines from haloprenes and 4-vinylpyridines.

Another object is to provide such a process which maximizes the yield of 4-(halocyclohex-3-enyl)pyridines.

Still another object is to provide such a process which maximizes the yield of 4-(4-halocyclohex-3-enyl)pyridines.

A further object is to provide novel processes for preparing derivatives of 4-(halocyclohex-3-enyl)pyridines.

These and other objects are attained by conducting the Diels-Alder reaction between a haloprene and a 4-vinylpyridine in the presence of boron trifluoride and, when appropriate, converting the resulting 4-(halocyclohex-3-enyl)pyridine to a desired derivative.

DETAILED DESCRIPTION

The haloprene utilized in the practice of the invention is generally chloroprene but can be any other haloprene, i.e., a 2-halobutadiene-1,3 in which the halo substituent may be chloro, bromo, fluoro, or iodo.

The 4-vinylpyridine reacted with the haloprene in the process of the invention is preferably 4-vinylpyridine itself but may be a ring-substituted 4-vinylpyridine bearing up to four innocuous substituents, such as alkyl, cycloalkyl, aralkyl, aryl, and aralkyl groups, optionally bearing halo, hydroxy, or amino substituents and/or optionally joined to the pyridine ring by an ether linkage; halo; cyano; carboxyl; carbalkoxy; carbamyl; nitrogen-containing heterocyclic groups, etc.—any aliphatic groups generally containing 1-6 carbons arranged in straight or branched chains.

The boron trifluoride catalyst may be boron trifluoride itself but is usually an etherate thereof, e.g., a diethyl, dipropyl, or dibutyl, etc., etherate. Preferably, it is a boron trifluoride/diethyl ether complex—the complex commonly known as boron trifluoride etherate. The amount employed of this ingredient is generally such as to provide a catalyst/4-vinylpyridine mol ratio in the range of about 1–2/1, preferably about 1.1/1.

Except for the use of the boron trifluoride catalyst, the process is conducted essentially in accordance with the teachings of Walter I, the teachings of which are incorporated herein by reference. Thus, it is preferred that the reactants be employed in substantially equimolar amounts, i.e., about 0.75–2, preferably about one, molar proportion of haloprene per molar proportion of the 4-vinylpyridine, and that they be reacted together at a temperature of about 100°–150° C., preferably about 130° C., under autogenous pressure, in a suitable solvent, preferably an aromatic hydrocarbon, such as xylene, which is liquid under the reaction conditions.

As in Walter I, the process results in the formation of a mixture of 4-(3-halocyclohex-3-enyl)pyridine and 4-(4-halocyclohex-3-enyl)pyridine isomers in a mol ratio of about 35:65. However, the process conducted in the presence of the boron trifluoride catalyst has the advantage of being virtually free of the dimerization and polymerization side reactions that reduce the total isomer yield to not more than about 20-30% in the earlier process; and it accordingly leads to total isomer yields of about 75-90% and 4-(4-halocyclohex-3-enyl)pyridine yields of about 45-50%.

When the process has been completed, as in Walter I, the 4-(halocyclohex-3-enyl)pyridine products may be separated if desired but are generally kept in admixture with one another when they are to be subjected to catalytic dehydrogenation to form the corresponding 4-(halophenyl)pyridines. Then, when other derivatives are desired, they may be subjected to the appropriate reactions, e.g., the reactions taught in Walter II, the teachings of which are incorporated herein by reference.

When the processes of Walter II are to be used, the object is generally to form derivatives of the 4-(4-halophenyl)pyridine, so it may be desirable first to separate it from any 4-(3-halophenyl)pyridine with which it is in admixture. However, if desired, a crude 4-(4-halophenyl)pyridine containing a 4-(3-halophenyl)pyridine impurity may be employed in these processes.

In general, when one or more of the processes of Walter II are to be employed, the 4-(4-halophenyl)pyridine—alone or in admixture with a 4-(3-halophenyl)pyridine—is nitrated to a 4-(4-halo-3-nitrophenyl)pyridine, preferably 4-(4-chloro-3-nitrophenyl)pyridine, which may then be reduced to a 4-(3-aminophenyl)pyridine, such as 4-(3-aminophenyl)pyridine itself. Then, when antibacterial agents, such as the 1-alkyl-1,4-dihydro-4-oxo-7-pyridinyl-3-quinolinecarboxylic acids of Lesher, Lesher et al., and Lesher and Carabateas, are desired, they—or their intermediates—may be prepared by subjecting the 4-(3-aminophenyl)pyridines to suitable reactions which may be conducted by known techniques. For example:

(1) the 4-(3-aminophenyl)pyridine may be reacted with a dialkyl ethoxymethylenemalonate to form a dialkyl 3-(4-pyridyl)anilinomethylenemalonate, which may be cyclized to an alkyl 1,4-dihydro-4-oxo-7-(4-pyridyl)-3-quinolinecarboxylate, which in turn may be N-alkylated to an alkyl 1-alkyl-1,4-dihydro-4-oxo-7-(4-pyridyl)-3-quinolinecarboxylate, which may then be hydrolyzed to a 1-alkyl-1,4-dihydro-4-oxo-7-(4-pyridyl)-3-quinolinecarboxylic acid, as in Lesher et al. and Lesher and Carabateas, (2) the 4-(3-aminophenyl)pyridine may be reductively alkylated, or it may be acylated and then reduced, as in Lesher, to form a 4-(3-alkylaminophenyl)pyridine, otherwise designated as a 3-(4-pyridyl)-N-alkylaniline, which may then be (a) subjected to the reaction steps of Lesher et al. and Lesher and Carabateas without the need for their N-alkylation step or (b) subjected to reaction with a cyclic alkylidenyl alkoxymethylenemalonate, etc., as in Lesher, to form the antibacterial agent, or (3) either of the above procedures may be terminated at the end of any step to recover a desired product for use in any other desired process, etc.

As in Walter II, when an acylated 4-(3-aminophenyl)pyridine is desired, it is sometimes convenient to combine the reduction and acylation steps, e.g., by reducing the 4-(4-halo-3-nitrophenyl)pyridine with hydrogen in the presence of sodium acetate, a palladium-on-carbon catalyst, and glacial acetic acid—a process which leads to a high yield of 4-(3-aminophenyl)pyridine at 60°–70° C. but which produces substantial yields of 4-(3-acetamidophenyl)pyridine when conducted for a sufficient time at temperatures near 80° C. Alternatively and more efficiently, 4-(3-acetamidophenyl)pyridine can be produced by including acetic anhydride in the reduction recipe.

The following examples are given to illustrate the invention and are not intended as a limitation thereof.

Unless otherwise indicated, the abbreviation CCHP is used in the examples to designate a mixture of 4-(3-chlorocyclohex-3-enyl)pyridine and 4-(4-chlorocyclohex-3-enyl)pyridine.

EXAMPLE I

A suitable reaction vessel was sequentially charged with a mixture of 1.5 g of 4-vinylpyridine in 5 ml of xylene, 4.3 g of boron trifluoride etherate, another 5 ml of xylene, and 4.5 ml of chloroprene to provide a reaction mixture containing 1.5 molar proportions of chloroprene and 2 molar proportions of boron trifluoride etherate per molar proportion of 4-vinylpyridine. The reaction mixture was maintained at 130°–140° C. for 10 hours and then evaporated to provide an oil. This oil was taken up in ether and successively extracted with four 75 ml portions of 1N HCl. The aqueous layers were combined, washed with ether, neutralized with aqueous NaOH to a pH of about 10, and extracted with methylene chloride. The methylene chloride layer was then dried, filtered, and evaporated to provide an oil which was pumped on a vacuum pump to give about 2.4 g of another oil. Analyses of the product showed that the process resulted in an 88% yield of 4-(4-chlorocyclohex-3-enyl)pyridine and 4-(3-chlorocyclohex-3-enyl)-pyridine in a mol ratio of 65:35 and having a purity of about 95%. There was no evidence that any dimerization or polymerization of the starting materials had occurred.

EXAMPLE II

Example I was essentially repeated except that the amount of chloroprene was reduced to 1.2 molar proportions, and the reaction was conducted at 140° C. for 5 hours. As in Example I, the process resulted in a high yield of CCHP, the yield of the 4-(4-chlorocyclohex-3-enyl)pyridine being in the range of 45–55%.

EXAMPLE III

Example I was essentially repeated except that the amounts of chloroprene and boron trifluoride etherate were reduced to one molar proportion and 1.1 molar proportions, respectively, and the reaction was conducted at 135° C. for 5 hours. The yield of the more desired CCHP isomer, i.e. 4-(4-chlorocyclohex-3-enyl)-pyridine, was 45–50%.

EXAMPLE IV

Example I was essentially repeated except that the amount of chloroprene was reduced to one molar proportion, the boron trifluoride etherate was replaced by one molar proportion of boron trifluoride as its hydroborofluoride salt, and the reaction was conducted at 130° C. for 5 hours. The yield of 4-(4-chlorocyclohex-3-enyl)pyridine was 42%.

COMPARATIVE EXAMPLE A

Example I was essentially repeated except that the boron trifluoride etherate was replaced with 2 molar proportions of triisobutylaluminum. The process resulted in the formation of no detectable amount of CCHP.

COMPARATIVE EXAMPLE B

Example I was essentially repeated except that the boron trifluoride etherate was replaced with 2 molar proportions of diethylaluminum chloride. The process resulted in the formation of chloroprene polymer.

COMPARATIVE EXAMPLE C

Example I was essentially repeated except that the boron trifluoride etherate was replaced with one molar proportion of lithium chloride, and chloroform was employed as the solvent. The process resulted in a yield of less than 10% of CCHP.

From the foregoing examples, it is apparent that Lewis acids in general are not effective as catalysts in the Diels-Alder reaction of the invention but that boron trifluoride is a very effective catalyst for the reaction.

It is obvious that many variations may be made in the products and processes set forth above without departing from the spirit and scope of this invention.

I claim:

1. In a process wherein a haloprene is reacted with a 4-vinylpyridine to form a 4-(halocyclohex-3-enyl)pyridine, the improvement which comprises conducting the reaction in the presence of a boron trifluoride catalyst.

2. The process of claim 1 wherein the haloprene is chloroprene.

3. The process of claim 1 wherein the 4-vinylpyridine is 4-vinylpyridine.

4. The process of claim 1 wherein the boron trifluoride catalyst is boron trifluoride.

5. The process of claim 1 wherein the boron trifluoride catalyst is a boron trifluoride etherate.

6. The process of claim 5 wherein the boron trifluoride etherate is a boron trifluoride/diethyl ether complex.

7. The process of claim 1 wherein the boron trifluoride catalyst is employed in an amount such as to provide about 1–2 mols of catalyst per mol of the 4-vinylpyridine.

8. The process of claim 1 wherein reaction is conducted in a liquid aromatic hydrocarbon solvent.

9. The process of claim 8 wherein the liquid aromatic hydrocarbon is xylene.

10. The process of claim 1 wherein substantially equimolar amounts of chloroprene and 4-vinylpyridine are reacted in the presence of about 1–2 molar proportions of the boron trifluoride catalyst and in a liquid aromatic hydrocarbon solvent.

11. The process of claim 10 wherein the boron trifluoride catalyst is boron trifluoride etherate.

12. The process of claim 10 wherein the amount of boron trifluoride catalyst employed is about 1.1 molar proportions per molar proportions of the 4-vinylpyridine.

13. The process of claim 12 wherein the boron trifluoride catalyst is boron trifluoride etherate.

14. In a process for preparing a 1-alkyl-1,4-dihydro-4-oxo-7-(4-pyridyl)-3-quinolinecarboxylic acid by (a) reacting a haloprene with a 4-vinylpyridine to form a 4-(4-halocyclohex-3-enyl)pyridine, (b) aromatizing the 4-(4-halocyclohex-3-enyl)-pyridine to a 4-(4-halophenyl)pyridine, (c) nitrating the 4-(4-halophenyl)-pyridine to a 4-(4-halo-3-nitrophenyl)pyridine, (d) reducing the 4-(4-halo-3-nitrophenyl)pyridine to a 4-(3-aminophenyl)pyridine, (e) converting the 4-(3-aminophenyl)-pyridine to a 3-(4-pyridyl)-N-alkylaniline, (f) reacting the 3-(4-pyridyl)-N-alkylaniline with a dialkyl ethoxymethylenemalonate to form a dialkyl 3-(4-pyridyl)-N-alkylanilinomethylenemalonate, (g) cyclizing the dialkyl 3-(4-pyridyl)-N-alkylanilinomethylenemalonate to an alkyl 1-alkyl-1,4-dihydro-4-oxo-7-(4-pyridyl)-3-quinolinecarboxylate, and (h) hydrolyzing the resultant ester; the improvement which comprises conducting the haloprene/4-vinylpyridine reaction in the presence of a boron trifluoride catalyst.

15. In a process for preparing a 1-alkyl-1,4-dihydro-4-oxo-7-(4-pyridyl)-3-quinolinecarboxylic acid by (a) reacting a haloprene with a 4-vinylpyridine to form a 4-(4-halocyclohex-3-enyl)pyridine, (b) aromatizing the 4-(4-halocyclohex-3-enyl)-pyridine to a 4-(4-halophenyl)pyridine, (c) nitrating the 4-(4-halophenyl)-pyridine to a 4-(4-halo-3-nitrophenyl)pyridine, (d) reducing the 4-(4-halo-3-nitrophenyl)pyridine to a 4-(3-aminophenyl)pyridine, (e) reacting the 4-(3-aminophenyl)-pyridine with a dialkyl ethoxymethylenemalonate to form a dialkyl 3-(4-pyridyl)anilinomethylenemalonate, (f) cyclizing the dialkyl 3-(4-pyridyl)anilinomethylenemalonate to an alkyl 1,4-dihydro-4-oxo-7-(4-pyridyl)-3-quinolinecarboxylate, (g) N-alkylating the alkyl 1,4-dihydro-4-oxo-7-(4-pyridyl)-3-quinolinecarboxylate to an alkyl 1-alkyl-1,4-dihydro-4-oxo-7-(4-pyridyl)-3-quinolinecarboxylate, and (h) hydrolyzing the resultant ester; the improvement which comprises conducting the haloprene/4-vinylpyridine reaction in the presence of a boron trifluoride catalyst.

16. The process of claim 14 wherein substantially equimolar amounts of chloroprene and 4-vinylpyridine are reacted in the presence of about 1–2 molar proportions of the boron trifluoride catalyst and in a liquid aromatic hydrocarbon solvent.

* * * * *